United States Patent
Garcia et al.

(10) Patent No.: US 11,253,454 B2
(45) Date of Patent: *Feb. 22, 2022

(54) METHOD FOR AFFECTING TOUCH

(71) Applicant: Johnson & Johnson Consumer Inc., Skillman, NJ (US)

(72) Inventors: Devin Garcia, Middlesex, NJ (US); Simarna Kaur, Neshanic Station, NJ (US); Janeta Nikolovski, Princeton, NJ (US); Louis DeRidder, Gansevoort, NY (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 226 days.

This patent is subject to a terminal disclaimer.

(21) Appl. No.: 15/913,160

(22) Filed: Mar. 6, 2018

(65) Prior Publication Data

US 2018/0256465 A1 Sep. 13, 2018

Related U.S. Application Data

(60) Provisional application No. 62/488,898, filed on Apr. 24, 2017, provisional application No. 62/469,666, filed on Mar. 10, 2017.

(51) Int. Cl.
| | |
|---|---|
| *A61K 8/37* | (2006.01) |
| *A61K 8/73* | (2006.01) |
| *A61Q 19/00* | (2006.01) |
| *A61K 8/92* | (2006.01) |
| *A61K 8/49* | (2006.01) |
| *A61K 8/06* | (2006.01) |

(52) U.S. Cl.
CPC .............. *A61K 8/37* (2013.01); *A61K 8/06* (2013.01); *A61K 8/4973* (2013.01); *A61K 8/731* (2013.01); *A61K 8/92* (2013.01); *A61Q 19/00* (2013.01); *A61Q 19/005* (2013.01); *A61Q 19/007* (2013.01); *A61Q 19/008* (2013.01)

(58) Field of Classification Search
CPC ... A61K 8/37; A61K 8/92; A61K 8/29; A61K 8/4973; A61K 8/731; A61K 8/922; A61K 8/375; A61K 8/06; A61Q 19/008; A61Q 19/005; A61Q 19/007; A61Q 19/00
See application file for complete search history.

(56) References Cited

U.S. PATENT DOCUMENTS

| | | | | |
|---|---|---|---|---|
| 2003/0064120 A1* | 4/2003 | Librizzi | ................. | A61K 36/13 |
| | | | | 424/736 |
| 2014/0356295 A1* | 12/2014 | Gerardi | .................. | A61K 8/922 |
| | | | | 424/43 |
| 2016/0317576 A1* | 11/2016 | Rosanoff | ................ | A61K 47/36 |
| 2018/0256464 A1* | 9/2018 | Garcia | ..................... | A61K 8/37 |

FOREIGN PATENT DOCUMENTS

| | | | |
|---|---|---|---|
| WO | WO-0178657 A1 * | 10/2001 | ............. A61Q 19/00 |
| WO | WO 2017/015275 A1 | 1/2017 | |

OTHER PUBLICATIONS

European Search Report dated Aug. 28, 2019 for Application No. 1917516.1.
Database GNPD [Online] Mintel; Oct. 31, 2016—Shang Mei Cosmetics "Moisturizing Cream (Baby Elephant Protection Series for Boys", XP002782005—Database accession No. 4356401 "the whole document".

* cited by examiner

*Primary Examiner* — Quanglong N Truong
(74) *Attorney, Agent, or Firm* — Laura A. Donnelly

(57) ABSTRACT

Leave-on compositions to be applied to the skin, which after five minutes post-application provides an improved low residue level, where the composition includes an emulsifier having a particular HLB value and an emollient present in a weight amount that is equal to or greater than the weight amount of the emulsifier.

6 Claims, 1 Drawing Sheet

METHOD FOR AFFECTING TOUCH

This application claims priority of the benefit of the filing of U.S. Provisional Application Ser. No. 62/469,666, filed Mar. 10, 2017 and U.S. Provisional Application Ser. No. 62/488,898, filed Apr. 24, 2017, the contents of which are hereby incorporated by reference in their entirety.

FIELD

The present invention is directed to a method of using a composition as a tool to affect touch between a human hand and the skin of a human, where the touch is an affective and soothing touch satisfying certain force or velocity factors.

BACKGROUND

It is desirable to apply compositions to the skin of humans, including adults as well as children. Composition forms include, for example, lotions, creams, gels and the like. Compositions are applied to the skin to help moisturize the skin, to leave the skin feeling smooth and healthy. Typically, such compositions are left on the surface of the skin without the need to wash or wipe the composition off the skin surface. It is typical, for example, for a caregiver, such as a parent or guardian, to apply lotion to the skin of a baby regularly. The moisture and barrier protection that such products provide to the skin of humans, including babies, may be desired.

However, some compositions are undesirable for a number of reasons. In some instances, compositions may not adequately spread onto the surface of the skin, whether due to the composition being too thick or too thin. In other instances, the compositions are undesirable because after application, the composition leaves an undesired residue on the surface of the skin.

Further, it has been discovered that a caregiver can touch a dependent, such as a baby or small child, with a certain touch, which generates emotional responses by the baby or small child. This touch falls within one or more of specific force ranges and specific velocity ranges. When the touch is too soft or slow, it does not register the appropriate response, and likewise when the touch is too fast or too forceful, it does not register the appropriate response. It is therefore desired to touch the skin of a baby or small child with a suitable, "affective" touch, where the touch falls within desired ranges.

The compositions of the present invention are suitable in that they provide an appropriate application onto the skin of a human, including adults and/or children, and do not suffer drawbacks associated with other compositions. The compositions of the present invention also allow for an adequate duration of massage onto the skin, while leaving low residue levels on the skin after use. Further, the methods incorporated from the present invention allow a caregiver to use the compositions of the present invention to touch the skin of a baby or small child at a desired rate and/or force, thereby providing a tool to achieve "affective" touch.

SUMMARY

In one aspect of the invention, there is a method of promoting affective and soothing touch by a caregiver to a child, including: The caregiver dispensing a predetermined amount of a composition onto one or more of the caregiver's hand or fingers and the child's skin, the composition having an emulsifier having an HLB value of between about 4 and about 10; and an emollient, where the emollient is present in a weight amount that is equal to or greater than the weight amount of the emulsifier; The caregiver using the caregiver's hand or fingers to apply the composition onto the surface of the child's skin for at least 20 seconds; whereby the step of applying is performed at a stroking force of from about 0.2N to about 2.0N and/or at a velocity of from about 1 cm/s to about 10 cm/s.

In another aspect, the invention includes a composition that helps promotes affective and soothing touch by a caregiver to a child, including: an emulsifier having an HLB value of between about 4 and about 10; and an emollient, where the emollient is present in a weight amount that is equal to or greater than the weight amount of the emulsifier; where the composition promotes application by a caregiver to the skin of a child at a stroking force of from about 0.2N to about 2.0N and/or at a velocity of from about 1 cm/s to about 10 cm/s.

DETAILED DESCRIPTION

Figure 1:
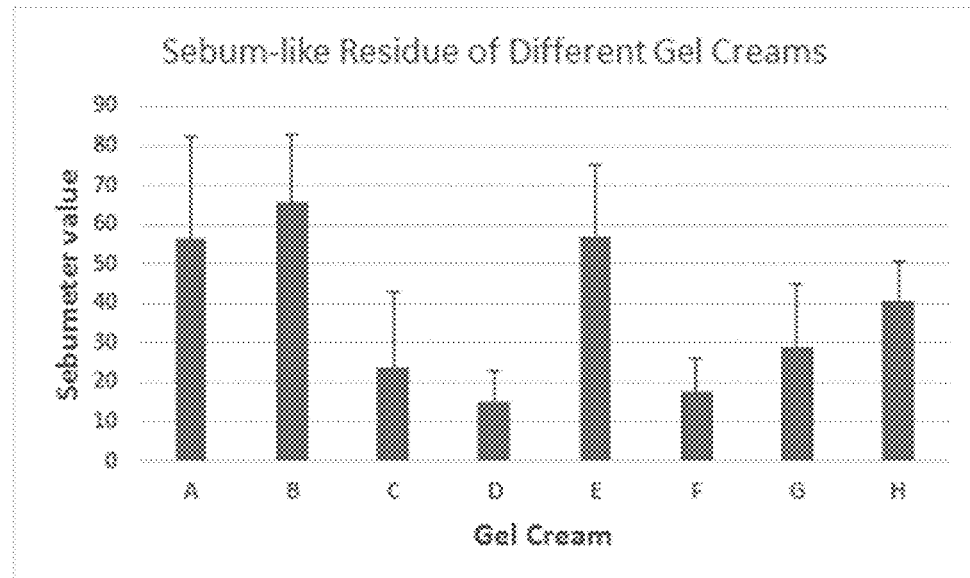
FIG. 1 is a graph showing the results of various gel creams tested for sebum-like residue on skin.

As used in this application, the term "composition" refers to a composition that is suitable to be applied to the surface of human skin, including adult skin as well as pediatric skin (baby and older children). Compositions in this invention may include lotions, creams, gels, or other similar formulations. The compositions of the present invention are intended to be applied to the skin by rubbing a desired amount of the composition onto the surface of skin with fingers or an application tool, where the rubbed-on composition is not removed from the skin by washing or wiping with a cloth or other removal tool. Therefore, the compositions of the present invention may be considered "leave-on" compositions, and are either free of skin irritating components, or any skin-irritating components in the compositions are present in such low levels that the skin of an average person is not irritated. Such "leave-on" compositions are in various formulation forms, such as lotions, creams and gels. The rheological properties of creams, gels and lotions are largely influenced by the ingredients and the formulation process. The ideal consistency of "leave-on" formulation as well as the consumer perception of the product as being pleasant is determined quantitatively directly on the skin in sensory tests with parameters such as structure or spreadability, measured in rotational and oscillatory tests with rheometers. By determining rheological parameters, it is possible to evaluate the applicative behavior of skin formulations (creams and lotions). Oscillation measurements, which correlate with the skin feel when applied, describe the structural properties of skin formulations, and viscosity curves evaluate the flow behavior and spreadability of skin formulations As used herein, the term "affective" touch, or alternatively, "soothing" touch, refers to the touch by a caregiver's hand to the skin of a dependent, such as a baby or a small child. The affective and/or soothing touch is characterized by a relatively slow, gentle stroke of the hand on the skin, which generates an emotional response of different haptic effect. The affective or soothing touch plays a vital role in social interactions between humans. The affective or soothing touch will be described in greater detail below with reference to certain measurable parameters, such as force and/or velocity.

In particular, the structure is a parameter for the evaluation of the skin formulation's behavior when it is extracted (e.g. pressed out of a tube) and for the skin feel, which is determined with an oscillation measurement, in the form of an amplitude sweep. Whereas the parameter G' (storage modulus) describes the elastic behavior of a sample, G" (loss modulus) represents the viscous portion. In the case when G' is above G" in the linear-viscoelastic range, the formulation exhibits gel-like behavior at the preset frequency, which means that the formulation will only start to flow when influenced by additional external forces. The gel-like behavior of the formulation is desirable as it is easily applicable on the skin and not drip off. The cream has a higher structural strength than lotion i.e. the values for storage and loss modulus of the cream are clearly higher than the values for the lotion. For instance, the G' value for lotion is from about 100 to about 400 Pa and the G' value for cream is from about 1000 Pa to about 6000 Pa.

The "leave-on" skin formulation (e.g. creams and lotions) generally show shear-thinning behavior, which can be evaluated using viscosity measurements; a low viscosity value correlates to an easier spreadability. However, the viscosity is not a constant value; it depends on the shear intensity and is described using the shear rate. A skin formulation of higher shear rates is applied more quickly and with more force than those of lower shear rates. The viscosity values of the skin cream are higher than lotions and it is expected that the difference in spreadability of the cream and lotion decreases with increasing shear stress. By way of example, in one aspect, at a given shear rate (e.g. 10 l/s), the composition may be a lotion having a viscosity of about 5 Pa·s at room temperature. In other aspects, the composition may be a gel, having a viscosity of about 1 Pa·s at room temperature. Viscosities may be dependent upon other parameters, including temperature and shear rates, and the aforementioned values are intended to be exemplary of lotions and gels.

The compositions of the present invention are to be applied to skin, in particular human skin. The "user" of the composition is the person that applies the composition onto skin, and therefore the user may be applying the composition onto his or her own skin or may apply the composition onto the skin of another individual. In some instances, the user applies a desired amount of composition onto the skin surface of a child or baby. In some instances, the user applies a desired amount of composition onto the skin surface of himself or herself.

The compositions of the present invention are intended to be applied to the skin by gently rubbing a desired amount of product onto the skin surface for a length of time that is sufficient to apply the composition across the target region of the skin surface. It may be desired that the user apply the composition using slow sweeping motions onto the skin, to allow for the product to be applied most effectively. In some instances, the amount of time to apply the composition is about 0.5 minutes to about 10 minutes, or from about 0.5 minutes to about 1 minute. In some embodiments, the application time may be as low as about 10 seconds, about 20 seconds, or about 45 seconds. In some aspects, the user is signaled to stop applying the composition because the composition turns transparent, or appears to become fully integrated into the skin, such as by feeling dry or feeling that the product is no longer present.

The compositions of the present invention are desirable in that they include products and methods of applying products that include a useful emulsifier blend, which leaves a low level of residue on the skin, and may also provide a desired after-feel. As used herein, the term "residue" refers to an oily/greasy film left behind on the skin after the product is applied to the skin and allowed to dry. As will be discussed below, the level of residue may be measured through the use of a sebumeter. The residue level may be measured at certain intervals, such as after 1 minute, after 2 minutes, after 3 minutes and/or after 5 minutes following application of the formulation by the fingers to the skin. In some aspects, residue measurements may be taken at multiple times after application to the skin. It is particularly useful that, after application and rubbing of the composition into the skin, the residue levels be desirably low. Particularly when a user is applying a composition to the skin of a baby, it is desired that the resulting feel of the baby's skin be as natural and residue-free as possible. As will also be described in greater detail below, the resulting product may also have a desired after-feel after rubbing the composition onto the skin.

In some aspects, the invention includes a composition that leaves a residue on the skin after application of less than about 40 ug/cm$^2$, as measured by a sebumeter. In other aspects, the invention may include a composition that leaves a residue on the skin after application that is less than about 30 ug/cm$^2$ as measured by a sebumeter.

In other aspects, the invention includes a composition that has a desirable after feel. "After feel" as used herein is defined as feel of the skin after application of a composition, with or without touching, usually measured at a specified time point. One such method of determining after feel is described in ASTM International. 2009. Standard Terminology Relating to Sensory Evaluations of Materials and Products, E253-09a. ASTM International, West Conshohocken, Pa. E253-09a.

In some aspects, "after feel" may be evaluated by measuring after-feel touch force using a finger TPS sensor, such as from Pressure Profile Systems, which is described in greater detail below. The desired level of after feel, measured by the finger TPS sensor, for products described in the present application is described below.

In other aspects, after-feel may be measured by a trained member of a sensory panel, who can assign a certain after-feel value to the user. For example, a sensory descriptive panel may be used for the evaluation of lotions, creams, serums, and ointments. As such, a team of trained panelists is calibrated to objectively assign intensity levels to a set of attributes that define and differentiate a product within a category. This set of attribute ratings is used to build the product's sensory profile which describes its use experience. In particular, the "after feel" level may be measured at certain intervals, such as after 1 minute, after 2 minutes, after 3 minutes, and/or after 5 minutes following application of the formulation by the fingers to the skin. In some aspects, after feel measurements may be taken at multiple times after application to the skin. The amount of material on the skin and its characterization is assessed by drawing the fingers across the application site and rating the level of after-feel felt between the fingers and the skin.

The product remaining on the skin, which may be described as a film, and the level of after-feel may be determined by the amount of formulation felt between the fingers and skin. Some characteristics described in the sensory test may include, for example: tactile detection of the following categories, which give exemplary descriptions and are not intended to be limiting:

Oily: thin coating on top; slippery and wet
Greasy: coating is thicker than oil; goopy and softer than wax; cushioned surface
Waxy: coating is thicker than oil; hard NEW candle feel; smooth
Silicone: thin coating; fills in the lines and finger ridges; smooth slip; can be powdery; may be slightly thicker than oil; resembling a new Teflon coated surface—smooth with a texture (e.g., not like a porcelain sink);
Powdery: dry, silky slip or wet, silky slip
Other: feel not defined above (e.g. sticky, glue-like; rubbery; sandy; chalky; etc.).

The sensory panel evaluates the feel for one or more of the above characteristics, and provides a resulting after feel level for each of the above. The after-feel analysis and resulting measurement help characterize the product after it has been applied. It is desired that the product have relatively lower scores for at least three of the characteristics described above, or at least four of the characteristics described above, particularly when compared to other lotions or leave-on bodily products.

In some aspects, the composition leaves the desired low level of residue on the skin described above, while also providing the desired level of after feel as described above. The desired composition results may be achieved, for example, through the use of the emulsifier and emollient blends described herein, coupled with the optional inclusion of powdered additives, as will be described below.

Components

Compositions of the present invention may include components that are suitable for use in a leave-on skin topical composition. By way of example, some components may include a carrier, such as water, silicone, polymers, preservatives, emulsifiers, emollients, fragrances, and other skin benefit agents. In some aspects, the compositions may include powdered additives, such as cellulose powders. As will be described below, it is particularly desirable to use a blend of an emulsifier and emollient, where the emulsifier has an HLB value within a desired range, and where the emollient is present in a greater amount than the emulsifier, based upon weight percentage of the final composition. While leave-on compositions are generally known, previous attempts have failed to achieve the present invention and results.

The present applicants have discovered that a leave-on product with desired residue levels can be achieved by using a particular amount and combination of components, including an emulsifier having a hydrophilic-lipophilic balance (HLB) value lower than about 9.5. In some embodiments, the emulsifier has an HLB value of lower than 9.0, and in some embodiments the HLB value is lower than 8.0. It may be desired that the HLB value of the emulsifier be greater than 3.0, or may be greater than 4.0. The composition most desirably is free of an emulsifier that has an HLB value of greater than 9.5, or free of an emulsifier having an HLB value of greater than 9.0, or free of an emulsifier having an HLB value of greater than 8.0, or free of an emulsifier having an HLB value of less than 3.0. In preferred embodiments, the composition only includes an emulsifier or emulsifiers that have the preferred HLB values, and therefore is free of emulsifiers having an HLB value outside of the aforementioned ranges. The HLB value of an emulsifier may be determined by calculating values for the different regions of the molecule. Emulsifiers may contain hydrophilic and lipophilic groups, and the proportion between the weight percentages of the hydrophilic and lipophilic groups is considered the HLB value. The HLB value is determined by calculating the molecular weight of the hydrophilic portion of the emulsifier and dividing by five.

In addition, it is preferred that the emulsifier be present in an amount of equal to or greater than 0.20% by weight of the composition. In some aspects, the emulsifier may be present in an amount of equal to or greater than 0.50% by weight of the composition, or present in an amount equal to or greater than 0.75% by weight of the composition. The emulsifier may be present in an amount of up to 2.0% by weight of the composition. As will be explained below, the present inventors have surprisingly found that increasing the amount of the present emulsifier in the composition from 0.75% to 2.0% (by weight) was found to either have no substantial effect, or have a beneficial effect on the resulting residue levels after application. In fact, the present inventors have surprisingly found that including only a low level of the emulsifier (e.g., 0.15% by weight of the composition) was found to increase residue levels after application. When an emulsifier having an HLB value outside of the preferred levels was used, by contrast, the resulting residue levels were higher and therefore less desirable.

Suitable emulsifiers have an HLB level described above. Emulsifiers having desired HLB values may include, for example, olive-derived emulsifiers, such as olivates. For example, one suitable emulsifier includes Olivem 1000 (sold by Hallstar), which is a combination of cetearyl olivate and sorbitan olivate. Other emulsifiers may include, but are not limited to, propylene glycol isostearate, glycol stearate, sorbitan sesquioleate, glyceryl stearate, lecithin, sorbitan oleate, sorbitan, monostearate NF, sorbitan stearate, sorbitan isostearate, steareth-2, oleth-2, glyceryl laurate ceteth-2, PEG-30 dipolyhydroxystearate, glyceryl stearate SE, sorbitan stearate, sucrose cocoate, PEG-4 dilaurate, methyl glucose sesquistearate, lecithin, PEG-8 dioleate, lecithin, sorbitan laurate, PEG-40 sorbitan peroleate, laureth-4, glycerol monostearate, propylene glycol ester of myristic acid, ester of palmitic acid, monoglyceride ester of myristic acid, monoglyceride ester of palmitic acid, monoglyceride ester of stearic acid, monoglyceride ester of oleic acid, ester of myristic acid, sorbitan ester of palmitic acid, sorbitan ester of stearic acid, sorbitan ester of oleic acid, ester of stearic acid, ester of oleaic acid, polyoxyethylene sorbitol, beeswax derivative, sorbitan sesquioleate, sorbitan sesquioleate, polyoxyethylenes orbitol, oleate, glycerol monostearate, polyoxyethylene sorbitol beeswax derivative s, propylene glycol fatty acid ester, sorbitan monooleate, sorbitan monooleate, propylene glycol monolaurate, propyleneglycolmonolaurate, propylene glycol fatty acid ester, sorbitan monostearate, sorbitan monostearate, diethylene glycol monostearate, diethylene glycol fatty acid ester, polyoxyethylene sorbitol beeswax derivative, diethylene glycol fatty acid ester, diethylene glycol fatty acid ester, polyoxyethylene sorbitol beeswax derivative, diethylene glycol, monolaurate (soap free), diethylene glycol fatty acid ester, diethylene glycol monolaurate (soap free), sorbitan monopahnitate, sorbitan monopahnitate, polyoxyethylene dioleate, tetraethylene glycol monooleate, polyoxypropylene mannitol dioleate, polyoxyethylene sorbitol lanolin, oleate derivative, polyoxyethylene sorbitol lanolin derivative, polyoxypropylene stearate, sorbitan monolaurate, and sorbitan monolaurate. As noted above, the emulsifier(s) used in the present invention should have a desired HLB value, described herein.

The present invention may also include an emollient. Emollients also known as moisturizers keep the skin moist by reducing water loss from the epidermis—the outer layer of skin and by providing a protective film. An emollient provides triple function to the skin, including occlusion, humectation and lubrication. Particularly, occlusion provides a layer of oil on the skin's surface to slow down water loss. Humectation enhances the surface of the skin's capacity to hold water. Lubrication reduces friction when anything rubs against the skin.

In some embodiments, the emollient is present in an amount greater than the emulsifier, and may be present in an amount that is greater than a 2:1 ratio of emollient to emulsifier (by weight). In some aspects, the emulsifier and emollient may be present in approximately equal amounts by weight. For example, suitable emollients include Isopropyl Palmitate. Other emollients may include, for example, mineral oil, lanolin, petrolatum, paraffin, beeswax, squalene, plant oils, such as coconut, jojoba, sesame, almond, and cottonseed, cetyl alcohol, olive oil (oleic acid), triethylhexanoin, shea butter, isopropyl myristate, C12-C15 alkyl benzoate, cocoglycerides and cocoa butter. Still other emollients may include massage oils, such as essential oils or carrier oils. Essential oils are thin oils with strong aromas which are extracts from the petals, root, bark, stem, leaves and aromatic portions of the plant extraction methods for example, steam distillation, cold-pressing and solvent extraction. These essential oils evaporate quickly and generally absorb quickly into the skin. Carrier oils, also called fixed oils, are vegetable oils that are used to dilute essential oils for maximum effectiveness and to minimize skin irritations or itching when used in undiluted forms. Massage oils often comprised of essential oils and carrier oils include, but not limited to; the Sea Buckthorn seed oil, the INCI name being Hippohae rhamnioides seed oil, the Pomegranate seed oil (*Punica granatum* seed oil), the Argan oil, the INCI name being *Argania spinosa* nut oil, the *Camellia* seed oil, the INCI name being *Camellia oleifera* seed oil, the Rosemary essential oil, the INCI name being *Rosmarinu officinalis*, the Tea Tree oil, the INCI name being *Melaleuca alternifolia* Leaf Oil, Lecithin, the INCI name being Lecithin, *Helichrysum* oil, the INCI name being *Helichrysum italicum* oil, Meadowfoam seed oil, the NCI name being *Limnanthes alba* seed oil, the Coffee *Arabica* oil, the NCI name being coffee *arabica* oil, and the d-alpha tochopherol is commonly known as Vitamin E.

The compositions of the present invention may include silicone-containing components, such as Dimethicone. Others include, but not limited to, alkylmethicone, cetyldimethicone, cyclomethiconedimethicone, laurylmethicone, and octyldimethicone ethoxyglucoside. Silicone-containing components may be present in an amount suitable for use in a leave-on composition, such as about 1% to about 5% by weight of the composition.

The compositions may include one or more polymeric components. Examples include but not limited to Acrylates/C 10-30 Alkyl Acrylate Crosspolymer, acrylate-alkyl acrylate copolymers, crosslinked polyacrylate polymers (including cationic and nonionic polymers), polyacrylamide polymers (including nonionic polyacrylamide polymers including substituted branched or unbranched polymers), polyacrylamide, isoparaffin and laureth-7, multi-block copolymers of acrylamides and substituted acrylamides with acrylic acids and substituted acrylic acids. Polymeric components may be present in any desired amounts, and for example, may be present in an amount of from about 0.1% to about 2% by weight of the composition.

Also included in the compositions may be preservatives and/or antimicrobial or antibacterial agents. Exemplary preservatives include phenoxyethanol. One such suitable preservative includes Euxyl PE 9010, sold by Schulke, which is a combination of ethylhexylglycerin and phenoxyethanol. Antimicrobial agents include, for example, Symdiol 68T (sold by Symrise), which is a blend of 1,2-hexanediol, caprylyl glycol, and tropolone. Other non-limiting examples of preservatives include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal or combinations thereof. Preservatives may be present in any desired amount, for example, from 0.1% to about 2% by weight of the composition.

Compositions of the present invention may include one or more powdered additives, which are added to the composition to provide a desired texture and deposition onto the skin. For example, powdered additives may include cellulose powders, such as cotton or pulp having an average length of from about 1 to about 1000 μm, a particle aspect ratio from about 1000 to about 2 and a thickness of from about 1 to about 1000 μm. The powdered additives may be hydrophobic, hydrophilic, or combinations thereof, and in some instances has the hydrophobicity or hydrophilicity associated with the powder in its natural state (e.g., not hydrophobically or hydrophobically modified). In one embodiment, the powdered additive may include regenerated cotton, sold under the trade name W325J White Cotton Flock (sold by Solvaira Specialties). The use of a powdered additive may be beneficial in providing a desired after-feel, which will be described in greater detail below. Therefore, in some aspects, the composition may provide a desired skin residue value and an after-feel level described below. The powdered additives may be present in the invention in an amount of from about 0.1% to about 3.0% by weight of the composition, and more desirably about 0.25% to about 1.0% by weight of the composition or about 0.5% by weight of the composition. In some aspects, however, the powdered additive may not be desired and therefore the composition may be free of the powdered additive.

Compositions may include fragrances, including fragrance oils or other fragrant components, or may be free of fragrances. If included, a fragrance may be present in any desired amount, and in some aspects is present from about 0.01% to about 1.0% by weight of the composition. The compositions may also include colorants or dyes, or may be free of dyes or colorants. When used, dyes or colorants may be present in an amount of from about 0.01% to about 1.0% by weight of the composition.

Compositions may include skin benefit agents, such as but not limited to, depigmentation agents; reflectants; amino acids and their derivatives; antimicrobial agents; allergy inhibitors; anti-acne agents; anti-aging agents; anti-wrinkling agents, antiseptics; analgesics; shine-control agents; antipruritics; local anesthetics; anti-hair loss agents; hair growth promoting agents; hair growth inhibitor agents, antihistamines; antiinfectives; anti-inflammatory agents; anticholinergics; vasoconstrictors; vasodilators; wound healing promoters; peptides, polypeptides and proteins; deodorants and anti-perspirants; medicament agents; skin firming agents, vitamins; skin lightening agents; skin darkening agents; antifungals; depilating agents; counterirritants; hemorrhoidals; insecticides; enzymes for exfoliation or other functional benefits; enzyme inhibitors; poison ivy products; poison oak products; burn products; anti-diaper rash agents; prickly heat agents; vitamins; herbal extracts; vitamin A and its derivatives; flavenoids; sensates; antioxidants; hair lighteners; sunscreens; anti-edema agents, neo-collagen enhancers, film-forming polymers, chelating agents; anti-dandruff/sebhorreic dermatitis/psoriasis agents; keratolytics; and mixtures thereof. The benefit agents useful herein may be categorized by their therapeutic benefit or their postulated mode of action. However, it is to be understood that the benefit agents useful herein may, in some circumstances, provide more than one therapeutic benefit or operate via greater than one mode of action. Therefore, the particular classifications provided herein are made for the sake of convenience and are not intended to limit the benefit agents to the particular application(s) listed.

The composition should include a suitable carrier, including water, in an amount desired to provide the intended thickness and feel of the composition. In some aspects, the carrier may be present in an amount of greater than or equal to 80% by weight of the composition, or greater than or equal to 85% by weight of the composition, or greater than or equal to 90% by weight of the composition.

The final compositions desirably have a pH that is suitable to be applied to the skin of human and remain on the skin of that human without washing or wiping off of the skin surface. pH modifying agents may therefore be incorporated into the composition, including, for example, sodium hydroxide. The final compositions may have any pH that is suitable for application onto the skin of a human, and may be from about 4.5 to about 7.0, or have a pH that is from about 5.0 to about 6.5, and more desirably from about 5.5 to about 6.0.

Residue Measurement Technique

As noted above, the present inventors have discovered a suitable composition that may be applied to the skin surface of a human, including a baby or small child, and leave a low residue level after application. Residue refers to the material remaining on the surface of the skin after application. While some products may leave some material on the skin after the composition is massaged and/or rubbed onto the skin, it is desirable that the perceivable residue on the skin be minimized and kept to a desired minimum. By way of example, it is known that oils applied to the skin leave a residue that is sticky/slippery or shiny. Powders are known to leave cake-like or grainy residue on the skin. An undesirable level of residue may make it difficult to get dressed after application.

The present inventions are beneficial in that they provide desired moisturization levels onto the skin, they allow for improved touching and massage, particularly when a caregiver applies compositions to the skin of another person or to a child. At the same time, however, the inventive compositions leave a desired residue level on the applied skin after the application is complete. Desired residue levels include low residue. As used herein, the term "low residue" means that the skin includes a low level of materials on the skin after application, which may be measured through a sebumeter or through the use of oil-absorbing sheets, which are measured before application and after by various methods, such as scanning and visual measurement, or through measuring weight before and after application. A sebumeter is an analytical device capable of quantitative measurement of deposition of oily materials onto skin from leave-on skin formulation as well as sebum-like residue levels. One suitable sebumeter is the SM815 Courage—marketed by Khazaka Electronic Koln. It has been discovered that the reduction of residue on a skin surface, particularly when the leave-on composition is applied by a caregiver to a small child or baby, is beneficial. Therefore, it is preferred that the level of residue be less than about 40 ug/cm$^2$ or less than about 30 ug/cm$^2$, or less than about 20 ug/cm$^2$, when 0.1 grams of the product is applied to the skin and rubbed onto the skin and allowed to dry, as measured by a sebumeter.

After-Feel Measurement Technique

In some aspects, the inventive compositions also leave the skin with a desired after-feel. In particular, when the applied skin is the skin of a child or infant, it may be desirable that the resulting skin have a soft and smooth after-feel. Therefore in some aspects of the invention, the composition may be capable of providing a smooth and soft after feel after application onto the skin. The after-feel may be measured by a method described above, outlined in ASTM International. 2009. Standard Terminology Relating to Sensory Evaluations of Materials and Products, E253-09a. ASTM International, West Conshohocken, Pa. E253-09a.

In some embodiments, the after-feel may be determined by following a protocol for after-feel force measurements using finger-TPS sensors (such as those sold by Pressure Profile Systems). One suitable protocol is described as follows:

Acclimation: the first, after-feel force measurements using finger sensors are conducted in a room with no windows, so that no outside visual stimuli are seen by the subjects during the study. Noise canceling headphones or other means of reducing external noise may be placed over the subject's ears or used, such as by playing white noise sound over the headphones or in the room. The subjects are allowed to become acclimated to these conditions for a desired period of time, such as 3 minutes, before beginning the test.

Testing: A plurality of areas are drawn on the volar side of the forearms of the subject. By way of example, one area may be approximately a 1.7 cm×15.0 cm rectangle, but other areas may be used so long as the area allows for the test to proceed as outlined below. There may be 2 areas, 3 areas, or more than 3 areas. One area on each arm is marked as bare skin rectangle for normalization of data. The subject puts on the finger-TPS sensor on the middle finger of their dominant hand first. The test coordinator ensures that the sensor is on the finger snugly, but not overly tight, and then applies a fixed amount (e.g., 0.20 g) of test product (lotion/cream, etc.) to the subject's volar forearm in the first box for about 30 seconds with uniformly timed parallel strokes. After waiting for approximately 2 minutes to allow the product to get absorbed into skin, the sensor may be calibrated (for each product) and the subject instructed to stroke their arm in the pre-selected area marked for bare skin to feel for softness of the skin. Then, the process is repeated in which the subject strokes within the remaining pre-marked areas pertaining to each of the applied products and feels for softness. The subjects may also complete questionnaires to rate the pleasantness and after-feel of skin in each pre-marked area.

The measured force provides one measurement of after-feel. It may be desired that the after feel for an inventive product has a measured maximum force of equal to or lower than about 5.0 N, or equal to or lower than about 3.0 N, or a measured average force of equal to or less than about 4.0 N, or equal to or less than about 3.0 N, or equal to or less than about 2.0 N.

Application Duration

In some aspects, the inventive compositions may be capable of being applied to the target skin within a desired length of time. By way of example, application may be completed in as little as about 0.5 minutes, or may be applied for about 10 minutes, or may be a time therebetween. Complete application, for purposes of this application, results when the applying person, who may be the same or may be different from the person to whom the composition is being applied, applies the product in a method similar to or identical to the method described below. It is to be understood that the method described below is exemplary and other methods of applying product onto the skin may be used. For example, more or less product may be applied and the surface area on the skin may be larger or smaller.

In one exemplary method, product is applied to the volar forearm of the user, and may be applied on both volar forearms. The product may be applied to any other skin region, including legs, chest, back, foot, hand, face, neck, shoulder, and other bodily regions. It is desired that about 0.10 grams to about 0.50 grams of product will be applied to a bodily region at a time. In preferred aspects, it is intended that about 0.10 grams of product will be applied to a skin region having a surface area of about 3 square inches (e.g., a 2"×1.5" region). More or less product may be applied as desired or needed. A user may dispense the desired amount of product into his or her hand or finger, or through the use of an applicator device. The user may wear a glove or may leave hands uncovered. The user applies the product onto the target site of the skin (which again, may be the user's own skin or may be the skin of another), and rub the product in an overlapping motion, which may be circular, linear, or random movement. The product is rubbed onto the skin for a desired time from about 10 seconds to about 5 minutes, or from about 10 seconds to about 1 minute, or desirably about 30 seconds. The user may stop rubbing the product when the user believes or feels that the product has been effectively absorbed onto the skin surface.

Method of Making Compositions

The invention includes methods of making compositions described herein. The compositions may be formed with the aid of heat or may be formed in a cooled or room temperature environment. In one aspect, it is beneficial to begin with a pre-mix of polymer(s) and optional powdered additives. The polymer(s) and optional powdered additives are mixed together until dispersed, and the pH may be modified to reach a desired target. For certain compositions, the target pH may be from about 5 to about 7, and may be about 5.5.

Heat may be used in the formation of the composition. In this aspect, the pre-mix may be heated to approximately 75-80° C., and while heating, emollients may be added and mixed throughout the pre-mix. Still under heat, the emulsifier may then be added and mixed. The composition may then begin to cool to a target temperature that is about 40° C. During the cooling, silicone, preservatives and other skin benefit agents may be added to the mixture. Once the mixture has cooled to a desired level, optional fragrances or other additives may then be added and mixed.

It may be desired to test the pH of the formulation after it is prepared, to ensure that the pH is within the desired range. Particularly for use as a topical skin product, and even more particularly for a topical skin product for use on babies and small children, the pH should be in the desired range.

Use of the Composition as a Tool for Touch

The compositions described above may be useful as a tool to allow caregiver to touch a baby or child (collectively referred to as a "child") with an "affective" (or "soothing") touch, as defined above. The touch between a caregiver and a child is important to establishing bonding, generating emotional responses, and overall growth of the baby or child. Examples of caregivers include parents, grandparents, guardians, and other individuals who provide care for the child. It is common for a caregiver to apply a product to the skin of the child, such as lotion or cream, for the purpose of healing or promoting skin health. However, the present inventors have discovered that the compositions described above may be useful in providing the caregiver with a tool for promoting an appropriate and specific type of touch between the hand/fingers of the caregiver and skin of the child.

Touching the skin of a child, as noted above, is important for a number of reasons, including the promotion of bonding between caregiver and child, added emotional and social benefits, and comfort and relaxation of the child. Touch can be measured in a number of different ways, including the force of the touch and the rate or velocity of the touch as the caregiver's hand/fingers move across the skin of the child. Different forces or rates of touch can provide different benefits. For example, a more forceful touch may be associated with massage. While a massaging touch may be helpful in some instances, the touch associated with the present invention is desirably a soothing or affective touch, which is distinct from massage touch.

The present invention relates to a method of affective or soothing touch, which is a softer touch than that associated with massage. The affective and soothing touch has a soft touch, but the force of touch must be at least at a level where the touch can be noticeably felt by the child and where the force of the touch has an impact. Too soft of a touch may either not be felt by the child or may be too soft to generate the emotional, social, and bonding impact desired. Similarly, too forceful of touch may not have the soothing impact that is desired under the present invention. Likewise, the soothing or affective touch of the present invention has a desired velocity, which is measured as the rate that the caregiver's hand or fingers moves across the skin surface of the child during application of a composition. Too slow or too fast of a touch will not provide the soothing impact desired by the present invention.

C-tactile fibers, as used herein, refer to a specialized system of unmyelinated c-type nerve fibers, which are highly sensitive to human interpersonal stroking touch. C-tactile afferents are found in hairy, but not in glabrous skin, and they respond optimally to a low force and velocity skin temperature stimulus/touch, typical of a caress. Selective C-tactile stimulation activates parts of the insular cortex, an area of the brain that has been implicated in the processing of positive emotional feelings.

C-tactile fiber activation may take place when the caregiver touches the skin of the child with a desired rate and/or force. In some instances, the activation may take place when the touch achieves only the desired rate, or only the desired force, or it may take place when the touch achieves both the desired rate and the desired force. A desired rate of touch is from about 1 cm/second to about 10 cm/second, or from about 1 cm/second to about 5 cm/second, or from about 2 cm/second to about 4 cm/second. A desired force is from about 0.2 N to about 2.0 N, or about 0.5 N to about 1.0 N.

The activity of C-tactile afferents may be measured for example by using a technique called Microneurography, in which very fine tungsten microelectrodes are inserted through the skin into a single nerve to capture its electrical impulses. Other less invasive ways to indirectly measure the activation of C-tactile fibers include: recording subjective ratings of touch pleasantness, implicit measures of affective state (facial electromyography), and autonomic arousal (heart rate) to determine whether C-tactile activation carries a positive affective value. Previously, a strong correlation has been shown between subjective pleasantness of touch and microneurography results showing activation of C-tactile fibers.

The stimulation of c-tactile fibers activates the fibers, and provides a perception of pleasantness and soothing to the touch. The child may demonstrate certain physiological responses, such as a lowered heart rate, an increased relaxation and deeper breathing, and/or certain behavioral characteristics, such as increased or elongated individual gazes toward the caregiver or stroking stimulus, increased interest expressed by the baby, increased expression of positive emotions such as smiles, or decreased expression of negative emotions and behaviors. This method may also evoke the mother to touch for longer periods of time than intended or express more positive feelings toward her baby and/or the product. Therefore, in certain aspects, the method is achieved by touching the skin of a child at a desired rate and/or velocity, thereby promoting at least one of a physiological response and/or a behavioral response, where the response demonstrates c-tactile fiber activation.

The compositions of the present invention are particularly useful in that they promote the caregiver touching the skin of the child in the ranges desired and explained above. As such, the compositions of the present invention may be considered a tool for achieving the intended level of touch, and therefore a tool for activating c-tactile fibers in a child. As can be appreciated, not all compositions would inherently and instinctively promote the desired touch level and response from the child. A thicker lotion would be likely to require a harder force and/or a slower rate of application, and a thinner lotion may increase the velocity to an undesirable level or lower the force too low. Given the rate of absorption of the inventive composition into the skin and the reduction in residue levels, the touch promoted by the present invention will drive a caregiver to touch at the desired and intended force and/or velocity levels.

The rate and/or force of touch of the caregiver to the skin of the child during application of the composition described herein may be measured with any commercially available means. The touch should last for at least a period of time sufficient to apply the composition to a selected surface of the child's skin, and may extend for a period of time beyond the application of composition to the skin surface, and may extend for a period of time beyond when the composition is rubbed into (or absorbed into or onto) the child's skin. The touch may continue for as long as desired until the composition is absorbed into the skin of the caregiver and/or child, or for as long as desired after application of the composition is complete. Touch may be for equal to or greater than: about 1 second, about 5 seconds, or about 10 seconds, about 20 seconds, about 30 seconds, about 40 seconds, about 50 seconds, or about 60 seconds. The touch may be longer than 60 seconds if desired.

EXAMPLES

The present applicants have prepared and examined a number of different compositions, which include varying levels and types of emulsifiers, emollients, and powdered additives. The resulting residue levels were tested after application for each test composition. The results of the residue measurements of Example 1 are displayed in the graph of FIG. 1. The results of residue measurements of Example 2 are displayed in the graph of FIG. 2.

It was surprisingly discovered that the type of emollient had an impact on the resulting residue level, while the type of emulsifier present had no significant impact. Further, it was found that the amount of emulsifier present had an effect on the residue levels, and even more surprising that, as the amount of low-HLB emulsifier was increased, the residue levels were reduced. One of ordinary skill in the art would have believed that increasing the amount of emulsifier would have increased the residue levels. Further, the effect of compositions including a powdered additive was measured, and it was found that the addition of a powdered additive had a reduction on the residue levels, although the reduction in the tests described below was not considered statistically significant for these tests.

The aforementioned tests and results are described below in the Examples. For each of the samples described in the below Examples, the same method of application and for measurement was used. The method is as follows: On the left and/or right volar forearms, 2"×1.5" rectangles were drawn, and 0.10 grams of product to be tested was applied to each rectangle five minutes before sebumeter measurements were taken. The sebumeter was set to have a reading of 0 when not applied to any surface, and if the sebumeter was not set appropriately, the system was calibrated. The tester applied one of the products with uniformly timed parallel strokes for 30 seconds. On the subject's arm, after 5 minutes of dry time, six sebumeter measurements were taken at random locations within the 2"×1.5" study area. The sebumeter was pressed onto the skin for 10 seconds for each measurement, and the tape was changed before each new measurement. The application and measuring method was repeated for each of the Samples. Each product was applied to five subjects and measurements were taken.

Example 1—Residue Calculations of Various Formulations

Comparison of Low-HLB Emulsifiers

Lotions A, B, and C were prepared. Lotion A was a comparative example, including 0.75% Stearic Acid (having an HLB of 15), 2% IPP, and 0.5% Cotton powder. Lotion B was a comparative example, including 0.75% cetyl alcohol (having an HLB of 15.5), 2% IPP, and 0.5% Cotton powder. Lotion C was an inventive example, including 0.75% olivem 1000 (having an HLB of 8-9), 2% IPP and 0.5% cotton powder. The compositions of Lotions A, B, and C are set forth in Table 1 below.

TABLE 1

Formulations of Lotions A, B, and C[1]

| | Lotion A | Lotion B | Lotion C |
| --- | --- | --- | --- |
| Ethylhexylglycerin | 0.06 | 0.06 | 0.06 |
| Phenoxyethanol | 0.54 | 0.54 | 0.54 |
| Dimethicone | 1.0 | 1.0 | 1.0 |
| Carbomer | 0.3 | 0.3 | 0.3 |
| Stearic acid | 0.75 | — | — |
| Cetyl alcohol | — | 0.75 | — |
| Water | 90.53 | 90.53 | 90.4 |
| Acrylates/C10-30 alkyl acrylate crosspolymer | 0.3 | 0.3 | 0.3 |
| Cetearyl olivate; sorbitan olivate | — | — | 0.75 |
| Sodium hydroxide | 0.17 | 0.17 | 0.15 |
| Glycerin | 3.0 | 3.0 | 3.0 |
| Isopropyl palmitate | 2.0 | 2.0 | 2.0 |
| 1,2-hexanediol; caprylyl glycol; tropolone | 0.5 | 0.5 | 0.5 |
| Cotton powder | 0.5 | 0.5 | 0.5 |
| Fragrance | 0.35 | 0.35 | 0.35 |

[1]The amounts are % by weight.

Lotion A was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 20% NaOH. The initial pH of Lotion A was 3.12, with a final pH of 6.46. The mixture was then heated, and while heating, glycerin and IPP were added. Once the temperature reached 80° C., stearic acid was added, and the mixture was mixed until uniform. The mixture was then cooled to 40° C., but once the mixture reached 50° C., dimethicone, 1,2-hexanediol; caprylyl glycol; tropolone, ethylhexylglycerin and phenoxyethanol were added. Once the temperature reached 40° C., fragrance was added. The final pH was then measured.

Lotion B was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 20% NaOH. The initial pH of Lotion B was 3.10, with a final pH of 6.38. The mixture was then heated, and while heating, glycerin and IPP were added. Once the temperature reached 80° C., cetyl alcohol was added, and the mixture was mixed until uniform. The mixture was then cooled to 40° C., but once the mixture reached 50° C., dimethicone, 1,2-hexanediol; caprylyl glycol; tropolone, ethylhexylglycerin and phenoxyethanol were added. Once the temperature reached 40° C., fragrance was added. The final pH was then measured.

Lotion C was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 50% NaOH. The initial pH of Lotion C was 3.04, with a final pH of 5.73. The mixture was then heated, and while heating, glycerin and IPP were added. Once the temperature reached 80° C., the cetearyl olivate/sorbitan olivate blend was added, and the mixture was mixed until uniform. The mixture was then cooled to 40° C., but once the mixture reached 50° C., dimethicone, 1,2-hexanediol; caprylyl glycol; tropolone, and the ethylhexylglycerin/phenoxyethanol blend were added. Once the temperature reached 40° C., fragrance was added. The final pH was then measured.

The method of application and measuring described above was used for Samples A, B, and C. Lotion A showed a resulting sebumeter value of 56±26 ug/cm$^2$. Lotion B showed a resulting sebumeter value of 65±17 ug/cm$^2$. Lotion C showed a resulting sebumeter value of 24±19 ug/cm$^2$. Therefore, as can be seen, Lotion C demonstrated a significantly lower resulting residue value as compared to Lotions A and B.

Comparison of Amount of Low-HLB Emulsifiers

Lotions D and E were prepared. Lotion D was an inventive example, including 0.75% olivem 1000 (having an HLB of 8-9), 2% IPP, and 0.5% Cotton powder. Lotion E was a comparative example, including 0.15% olivem 1000 (having an HLB of 8-9), 2% IPP, and 0.5% Cotton powder. The compositions of Lotions D and E are set forth in Table 2 below.

TABLE 2

Formulations of Lotions D and E

| | Lotion D | Lotion E |
| --- | --- | --- |
| Ethylhexylglycerin | 0.06 | 0.06 |
| Phenoxyethanol | 0.54 | 0.54 |

TABLE 2-continued

Formulations of Lotions D and E

| | Lotion D | Lotion E |
| --- | --- | --- |
| Dimethicone | 1.0 | 1.0 |
| Carbomer | 0.3 | 0.3 |
| Water | 89.2 | 91.15 |
| Acrylates/C10-30 alkyl acrylate crosspolymer | 0.3 | 0.3 |
| Cetearyl olivate; sorbitan olivate | 2.0 | 0.15 |
| Sodium hydroxide | 0.17 | 0.15 |
| Glycerin | 3.0 | 3.0 |
| Isopropyl palmitate | 2.0 | 2.0 |
| 1,2-hexanediol; caprylyl glycol; tropolone | 0.5 | 0.5 |
| Cotton powder | 0.5 | 0.5 |
| fragrance | 0.35 | 0.35 |

Lotion D was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 20% NaOH. The initial pH of Lotion D was 2.96, with a final pH of 6.70. The mixture was then heated, and while heating, glycerin and IPP were added. Once the temperature reached 80° C., the cetearyl olivate/sorbitan olivate blend was added, and the mixture was mixed until uniform. The mixture was then cooled to 40° C., but once the mixture reached 50° C., dimethicone, 1,2-hexanediol; caprylyl glycol; tropolone, and the ethylhexylglycerin/phenoxyethanol blend were added. Once the temperature reached 40° C., fragrance was added. The final pH was then measured.

Lotion E was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 20% NaOH. The initial pH of Lotion E was 3.30, with a final pH of 6.16. The mixture was then heated, and while heating, glycerin and IPP were added. Once the temperature reached 80° C., the cetearyl olivate/sorbitan olivate blend was added, and the mixture was mixed until uniform. The mixture was then cooled to 40° C., but once the mixture reached 50° C., dimethicone, 1,2-hexanediol; caprylyl glycol; tropolone, and the ethylhexylglycerin/phenoxyethanol blend were added. Once the temperature reached 40° C., fragrance was added. The final pH was then measured.

The method of application and measuring described above was used for Samples D and E. Lotion D showed a resulting sebumeter value of 24±19 ug/cm$^2$. Lotion E showed a resulting sebumeter value of 57±18 ug/cm$^2$. Therefore, as can be seen, Lotion D demonstrated a significantly lower resulting residue value as compared to Lotion E, as well as compared to Lotions A and B from Example 1.

Comparison of Emollients

Lotions F and G were prepared. Lotion F was an inventive example, including 0.75% olivem 1000 (having an HLB of 8-9), 2% cocoglycerides, and 0.5% Cotton powder. Lotion G was an inventive example, including 0.75% olivem 1000 (having an HLB of 8-9), 2% mineral oil, and 0.5% Cotton powder. The compositions of Lotions F and G are set forth in Table 3 below.

TABLE 3

Formulations of Lotions F and G

| | Lotion F | Lotion G |
|---|---|---|
| Ethylhexylglycerin | 0.06 | 0.06 |
| Phenoxyethanol | 0.54 | 0.54 |
| Dimethicone | 1.0 | 1.0 |
| Carbomer | 0.3 | 0.3 |
| Water | 90.53 | 90.53 |
| Acrylates/C10-30 alkyl acrylate crosspolymer | 0.3 | 0.3 |
| Cetearyl olivate; sorbitan olivate | 0.75 | 0.75 |
| Sodium hydroxide | 0.17 | 0.17 |
| Glycerin | 3.0 | 3.0 |
| Mineral oil | — | 2.0 |
| cocoglycerides | 2.0 | — |
| 1,2-hexanediol; caprylyl glycol; tropolone | 0.5 | 0.5 |
| Cotton powder | 0.5 | 0.5 |
| fragrance | 0.35 | 0.35 |

Lotion F was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 20% NaOH. The initial pH of Lotion F was 3.03, with a final pH of 6.64. The mixture was then heated, and while heating, glycerin and cocoglycerides were added. Once the temperature reached 80° C., the cetearyl olivate/sorbitan olivate blend was added, and the mixture was mixed until uniform. The mixture was then cooled to 40° C., but once the mixture reached 50° C., dimethicone, 1,2-hexanediol; caprylyl glycol; tropolone, and the ethylhexylglycerin/phenoxyethanol blend were added. Once the temperature reached 40° C., fragrance was added. The final pH was then measured.

Lotion G was prepared by the following procedure: Water was added to a beaker, and Acrylates/C10-30 alkyl acrylate crosspolymer, carbomer, and cotton powder were slowly sprinkled into the water. The mixture was mixed until fully dispersed/hydrated. The pH was then adjusted with 20% NaOH. The initial pH of Lotion G was 2.93, with a final pH of 6.18. The mixture was then heated, and while heating, glycerin and mineral oil were added. Once the temperature reached 80° C., the cetearyl olivate/sorbitan olivate blend was added, and the mixture was mixed until uniform. The mixture was then cooled to 40° C., but once the mixture reached 50° C., dimethicone, 1,2-hexanediol; caprylyl glycol; tropolone, and the ethylhexylglycerin/phenoxyethanol blend were added. Once the temperature reached 40° C., fragrance was added. The final pH was then measured.

The method of application and measuring described above was used for Samples F and G. Lotion F showed a resulting sebumeter value of 18±9 ug/cm$^2$. Lotion G showed a resulting sebumeter value of 29±16 ug/cm$^2$. Therefore, as can be seen, Lotions F and G demonstrated comparable residue values to themselves and also Lotions D and C, from the above Examples. Lotions F and G therefore show that a desired low residue can be maintained even when the emollients used were changed.

Composition without Powdered Additive

Lotion H was prepared. Lotion H was an example removing the optional powdered additive, including 0.75% olivem 1000 (having an HLB of 8-9) and 2% IPP, and being free of Cotton powder. The composition of Lotion H is set forth in Table 4 below.

TABLE 4

Formulations of Lotion H

| | Lotion H |
|---|---|
| Ethylhexylglycerin | 0.06 |
| Phenoxyethanol | 0.54 |
| Dimethicone | 1.0 |
| Carbomer | 0.3 |
| Water | 91.03 |
| Acrylates/C10-30 alkyl acrylate crosspolymer | 0.3 |
| Cetearyl olivate; sorbitan olivate | 0.75 |
| Sodium hydroxide | 0.17 |
| Glycerin | 3.0 |
| Isopropyl palmitate | 2.0 |
| 1,2-hexanediol; caprylyl glycol; tropolone | 0.5 |
| fragrance | 0.35 |

Lotion H was prepared by the following procedure: Water was added to a beaker, and Acrylates/C10-30 alkyl acrylate crosspolymer, and carbomer were slowly sprinkled into the water. The mixture was mixed until fully dispersed/hydrated. The pH was then adjusted with 20% NaOH. The initial pH of Lotion H was 2.9, with a final pH of 6.48. The mixture was then heated, and while heating, glycerin and IPP were added. Once the temperature reached 80° C., the cetearyl olivate/sorbitan olivate blend was added, and the mixture was mixed until uniform. The mixture was then cooled to 40° C., but once the mixture reached 50° C., dimethicone, 1,2-hexanediol; caprylyl glycol; tropolone, and the ethylhexylglycerin/phenoxyethanol blend were added. Once the temperature reached 40° C., fragrance was added. The final pH was then measured.

The method of application and measuring described above was used for Sample H. Lotion H showed a resulting sebumeter value of 30±10 ug/cm$^2$. This shows that the resulting composition without the cotton particles can still provide a suitable residue level, the residue level was higher than those of Lotions C and D (and F and G). Therefore, the lack of cotton particles within the composition demonstrated a higher level of residue than compositions including the cotton particles, but still provides a residue level that is low. In aspects where the residue level is desirably about 40 ug/cm$^2$ or less, the compositions without cotton particles is satisfactory.

As described above, however, the inclusion of cotton particles or other similar particles may be desired and may add to providing a desired after-feel as well as achieving a low residue level.

Summary of Example 1

Figure 2:
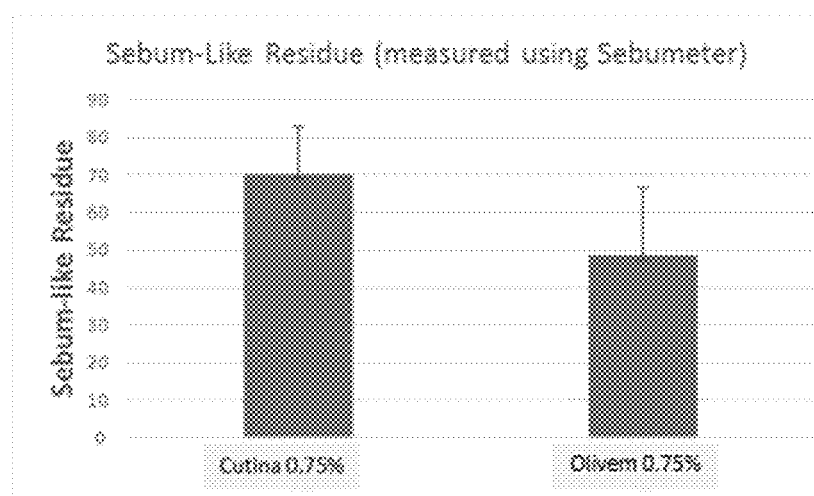
FIG. 2 is a graph showing the results of residue testing conducted on two creams with differing emulsifiers.

The results of the tests as set forth in FIG. 1 demonstrate the results of residue levels of Lotions A-H. As can be seen, Formulations A, B, and E showed the highest level of sebum-like residue. This shows that the substitution of stearic acid and cetyl alcohol, which have HLB values of 15 and 15.5, respectively, produced significantly more residue than compositions including the emulsifier in the desired HLB range. Further, it can be seen that by reducing the amount of the low HLB emulsifier to a level of 0.15% (Example D), the amount of residue was actually increased. When the emulsifier was increased to a level of 0.75% and 2.0%, the residue levels were seen to have dropped.

This was quite surprising, since typically, in a leave-on formulation emollients are expected to play a key role in product residue on skin. In our study, it was observed that the HLB-value of the emulsifier and its dose were showing a direct correlation with the amount of residue that the formulation left on skin, which was surprising. Overall, the present inventors have identified a range of HLB values for the emulsifiers that could result in the formulation leaving a low residue on skin and optionally a desired after-feel level. One would believe that increasing the amount of the emulsifier, even with the described desired HLB value, the level of fatty acid or oily substance would be increased in the formulation, which means more of this material would be left on skin after application, thus increasing the residue. However, this did not occur, and instead a lower residue level remained.

Further surprising were the results seen when the emollient was substituted for other emollients, as no significantly different residue result was seen when IPP, mineral oil, or cocoglycerides were used. This demonstrates that the use of the specific HLB-value emulsifier in amounts described above provided desired residue levels after application.

Example 2—Residue Calculations with Varying Emulsifiers

It was desired to test emulsifiers that have low HLB values to determine variations or trends. To achieve this, two formulations were prepared, the first including an emulsifier having an HLB value of about 3.9 (Cutina® GMS V, Glyceryl Stearate, manufactured by BASF) and the second having an emulsifier of about 8-9 (Olivem 1000). The test was conducted to determine if the lower HLB emulsifier would have an even greater residue-reducing effect than the emulsifier having a still low (but higher respectively) HLB value.

TABLE 5

Formulation of Lotion K[2]

| | Lotion K |
|---|---|
| Ethylhexylglycerin | 0.06 |
| Phenoxyethanol | 0.54 |
| Dimethicone | 1.0 |
| Carbomer | 0.3 |
| Water | 90.53 |
| Acrylates/C10-30 alkyl acrylate crosspolymer | 0.3 |
| Cutina GMS V (Glyceryl Stearate) | 0.75 |
| Sodium hydroxide | 0.17 |
| Glycerin | 3.0 |
| Isopropyl palmitate | 2.0 |
| Cotton powder | 0.5 |
| 1,2-hexanediol; caprylyl glycol; tropolone | 0.5 |
| fragrance | 0.35 |

[2]Data for Lotion I and Lotion J are not included as these lotions are not relevant to the present invention.

TABLE 6

Formulation of Lotion L[3]

| | Lotion L |
|---|---|
| Ethylhexylglycerin | 0.06 |
| Phenoxyethanol | 0.54 |
| Dimethicone | 1.0 |
| Carbomer | 0.3 |
| Water | 90.53 |
| Acrylates/C10-30 alkyl acrylate crosspolymer | 0.3 |
| Olivem 1000 | 0.75 |
| Sodium hydroxide | 0.17 |
| Glycerin | 3.0 |
| Isopropyl palmitate | 2.0 |
| 1,2-hexanediol; caprylyl glycol; tropolone | 0.5 |
| Cotton powder | 0.5 |
| fragrance | 0.35 |

[3]Although Lotion L and Lotion C contain the same ingredients in the same amounts, the sebumeter results for Lotion L and Lotion C differ slightly as Lotion L and Lotion C were tested at different times using different subject.

Lotions K and L were separately applied to the skin of 5 individuals using the method described below. The level of residue on the skin was measured using the same sebumeter as in Example 1 above.

On the left and right volar forearms, 2"×1.5" rectangles was drawn, and 0.15 grams of the product was applied to each rectangle five minutes before sebumeter measurements were taken. The sebumeter was tested to ensure a reading of 0 when it was not applied to any surface, and if it was not zero then the system was calibrated. The user applied the product tested with uniformly timed parallel strokes for 30 seconds. On the subject's arm, after 5 minutes of dry time, six sebumeter measurements were taken at random locations within the 2"×1.5" study area. The sebumeter was pressed onto the skin for 10 seconds each measurement, and the tape was changed before each new measurement. The method of application and measurement was repeated for each of the samples The method of application and measuring described above was used for Samples K and L. Lotion K showed a resulting sebumeter value of 70±13 ug/cm$^2$. Lotion L showed a resulting sebumeter value of 48±18 ug/cm$^2$, thus showing that the composition including an emulsifier having the HLB value of about 8-9 demonstrated a lower residue on the skin than the emulsifier having an HLB value of about 3.9.

This result was surprising, since it had previously been thought that the lower the HLB value, the lower the resulting level of residue would be on the skin. However, this was determined to be incorrect, and the present applicants have discovered that the compositions of the present invention provide an impressive reduction in the level of residue on the skin. The desirability of low residue on the skin is described above, and therefore the second formulation in this Example was determined to be more effective.

Comparison of Amount of Low-HLB Emulsifiers

Comparative Example (Lotion M) containing emulsifier Cremophor A6 (Ceteareth-6 (and) Stearyl Alcohol, BASF) exhibited a much higher residue. Lotion M was prepared using Cremophor (having an HLB 10-12), and lotion N (inventive) was prepared with Olivem 1000 (having an HLB 8-9).

The residue for Lotion M and Lotion N, shown in tables 7-8 below, were measured by the same test procedure as described in Example 1 above.

TABLE 7

Formulations of Lotion M

| | Lotion M |
|---|---|
| Ethylhexylglycerin | 0.06 |
| Phenoxy ethanol | 0.54 |
| Dimethicone | 1.0 |

TABLE 7-continued

| | |
|---|---|
| Carbomer | 0.3 |
| Water | 90.53 |
| Acrylates/C10-30 alkyl acrylate crosspolymer | 0.3 |
| Cremophor A6 | 0.75 |
| Sodium hydroxide | 0.17 |
| Glycerin | 3.0 |
| Isopropyl palmitate | 2.0 |
| 1,2-hexanediol; caprylyl glycol; tropolone | 0.5 |
| Cotton powder | 0.5 |
| Fragrance | 0.35 |

Formulations of Lotion N

| | Lotion N |
|---|---|
| Ethylhexylglycerin | 0.06 |
| Phenoxy ethanol | 0.54 |
| Dimethicone | 1.0 |
| Carbomer | 0.3 |
| Water | 90.53 |
| Acrylates/C10-30 alkyl acrylate crosspolymer | 0.3 |
| Olivem 1000 | 0.75 |
| Sodium hydroxide | 0.17 |
| Glycerin | 3.0 |
| Isopropyl palmitate | 2.0 |
| 1,2-hexanediol; caprylyl glycol; tropolone | 0.5 |
| Cotton powder | 0.5 |
| fragrance | 0.35 |

The method of application and measuring described above for Example 1 was used for Samples M and N. Lotion M showed a resulting sebumeter value of 32±13 ug/cm². Lotion N showed a resulting sebumeter value of 18±12 ug/cm². Therefore, as can be seen, Lotion N demonstrated a significantly lower resulting residue value as compared to Lotion M.

What is claimed is:

1. A method of promoting affective and soothing touch by a caregiver to a child, comprising:
    a. the caregiver dispensing a predetermined amount of a composition onto the caregiver's hand or fingers and/or the child's skin, the composition comprising an emulsifier having an HLB value of between about 4 and about 10; and an emollient, wherein said emollient is present in a weight amount that is equal to or greater than the weight amount of the emulsifier;
    b. the caregiver using the caregiver's hand or fingers to apply the composition onto a selected surface of the child's skin for a period of time sufficient to apply the composition to a selected surface of the child's skin;
    whereby the step of applying is performed at a stroking force of from about 0.2N to about 2.0N and/or at a velocity of from about 1 cm/s to about 10 cm/s;
    wherein the composition comprises from about 0.20% to about 0.75% by weight of emulsifier, wherein said emulsifier is an olivate, wherein said olivate is a combination of cetearyl olivate and sorbitan olivate; an emollient isopropyl palmitate, wherein said isopropyl palmitate is present in a weight amount that is equal to or greater than the weight amount of the olivate; and cellulose powder, wherein the cellulose powder comprises regenerated cotton powder, wherein said regenerated cotton powder is present in an amount of about 0.1% to about 3.0% by weight of the composition, wherein said cellulose powder is dispersed throughout said composition.

2. The method of claim 1, wherein the selected surface of the child's skin includes a region of skin in which there is hair present.

3. The method of claim 1, wherein the step of applying the composition activates at least one c-tactile fiber in the selected surface of the child's skin.

4. The method of claim 3, wherein activation of c-tactile fiber is demonstrated by at least one of: higher perception of pleasantness of the touch, lowered heart rate and increased relaxation, recording and measuring affective state by facial electromyography, and higher degree of behavioral engagement.

5. The method of claim 4, wherein the higher degree of behavioral engagement comprises at least one period of longer individual gaze by the child at the stroking stimulus.

6. The method of claim 1, wherein said composition is free of emulsifier having an HLB value of below 4 or above 10.

* * * * *